United States Patent [19]

Shaber et al.

[11] 4,365,895

[45] Dec. 28, 1982

[54] METHOD, APPARATUS AND FILM STRIP OF PARTICULAR DESIGN FOR RAPID TEST OF A FILM PROCESSOR

[75] Inventors: Gary S. Shaber, Villanova, Pa.; Charles W. Buenzli, Jr., Richardson, Tex.

[73] Assignee: Probex, Inc., Villanova, Pa.

[21] Appl. No.: 212,742

[22] Filed: Dec. 3, 1980

[51] Int. Cl.³ .................... G01N 21/86; G01N 21/59
[52] U.S. Cl. ................................... 356/444; 250/559; 354/298
[58] Field of Search .............. 356/443, 444, 434, 445, 356/226; 250/559–561, 571; 354/297, 298, 299, 20

[56] References Cited

U.S. PATENT DOCUMENTS

3,995,959 12/1976 Shaber ................................ 356/443
4,239,395 12/1980 Modisette ........................... 356/443

Primary Examiner—Bruce Y. Arnold
Attorney, Agent, or Firm—Ratner & Prestia

[57] ABSTRACT

Apparatus and method for evaluation of a film processor, particularly an x-ray film processor, based on a photodetector signal sequentially indicating the optical density of graded density test areas on a developed film and comparing the output thereof to a preselected voltage relating to the acceptable/too dark threshold of an unexposed or base fog area, the acceptable or too light threshold of a maximum density or dark area and the acceptable/too light and acceptable/too dark threshold of a medium density test area. Sequence testing of the graded density areas is functionally related on a single film strip to timing marks, adapted to be read by photodetector and timing circuitry, the timing marks and graded density test areas being linearly spaced and relatively disposed along the length of film strip.

13 Claims, 8 Drawing Figures

METHOD, APPARATUS AND FILM STRIP OF PARTICULAR DESIGN FOR RAPID TEST OF A FILM PROCESSOR

INTRODUCTION AND BACKGROUND

This invention pertains to an improved method and means for rapidly determining the operational status of a film processor, such as an x-ray film developer. More particularly, this invention pertains to such means and method wherein the proper operation of the developer or identified malfunctions of the developer can be confirmed reliably and efficiently.

With the increasing concern for minimizing x-ray exposure, the need has grown for quickly and accurately determining whether an x-ray developing apparatus or processor is functioning properly. If it is not, the x-ray may have to be retaken.

To a less extent, method and means for determining the operational status of other types of film processors would also be desirable. For that reason, the present invention will be described herein with reference to photograhic film and film processors generally, although the most immediate and well defined need to which the present invention is addressed is that involving x-ray film processing.

In developing photographic films, it is important to closely monitor a number of critical parameters, such as for example, the temperature and strength of the chemical developers employed, to insure that the proper film densities are achieved. It is sometimes possible to determine that one or more of these parameters is not correct by inspection of a normally developed film, but without more information, identification of the specific cause of improper processing is difficult.

Manual comparison of a developed film (produced from calibrated exposure of sections of the film) to predetermined density standards and analysis of the results of this comparison (sometimes requiring trial and error adjustments of the processor) is presently relied upon to determine the operational status of x-ray film processors in some hospitals. The general object of the present invention is to provide a method and apparatus for performing this function automatically.

The only known prior art method and means for performing such function automatically is that disclosed and claimed in U.S. Pat. No. 3,995,959 of Gary S. Shaber, one of the co-inventors herein. That patent discloses and claims a system wherein a film having a test pattern including at least three areas of graded density, one of which is an unexposed or base fog area, is developed in the processor to be checked. The developed film is then tested in a device including three light sources and photo detectors focused on the three graded density areas (the proper graded density of which is predetermined and related to a preselected signal in the photodetector associated with that area) in order to determine whether each graded density area, as developed, is too light or too dark or within the specified limits.

Various combinations of the output indications for the graded density areas being too light, acceptable, or too dark are electronically integrated to produce output signals indicative of either proper operation of the processor or specified malfunctions of the processor such as "developer underreplenished", "developer temperature too low", "developer temperature too high", and "developer contaminated".

The apparatus disclosed for carrying out that process in the '959 patent is somewhat inefficient, however, because of the continuing necessity to maintain the relative calibration of the various light sources and photodetectors and the necessarily duplicative circuits in the device.

It is therefore a general object of the present invention to provide a more efficient and more reliable method and means for determining the operational status of a film processor utilizing evaluation of a plurality of graded density test areas in a developed film, comparison of these graded densities to preselected standards and interrelating the results of that test to confirm proper process or operation or specific problems in the processor.

A more specific object of the present invention is to provide an expeditious method, means and film strip design adapted to indicate, very rapidly, the operational status of an x-ray film processor.

BRIEF DESCRIPTION OF INVENTION

In accordance with the present invention, these objects are met by a device for comparing the density of a series of graded density test areas on a test film, one of which establishes a base point in an unexposed area of the film, in which the density is referred to as "base fog". That is then correlated to a reference level or zero point of the density comparator, preferably the 100% transmission point of the apparatus. The remaining graded density areas are then compared also to preselected ratiometric values which are a function of the zero point and which are related to predetermined levels of graded density indicative of proper development of the film. The apparatus in accordance with this invention utilizes a single light source and photodetector which measures the graded density areas sequentially so that calibration of a multiplicity of light sources and photodetectors is not necessary.

In particular, the photocurrent created by the density being measured in each area of the graded density film is compared to a reference current from a precision divider string by the same optics and operational amplifier circuit used in setting the 100% transmission level. The apparatus is self-compensating for long term drifts in the measuring circuit. Thus, the only accuracy determining considerations in the circuit are the stability of the precision resistor divider network, the short term drift of the operational amplifiers, the linearity of the photodetector, and the drift of the sample and hold circuit.

In the preferred form of the present invention, the graded density areas of the film are arranged in a linearly disposed path, along which is disposed a timing signal track by which the apparatus is sequenced to different stages of the test mode. Such a film strip with the linearly arranged graded density areas and associated timing signal track means is an important aspect of the preferred embodiment of the present invention.

For a better understanding of this invention, reference may be made to the detailed description thereof which follows, taken in conjunction with the accompanying claims and drawings, in which like reference numerals designate like parts.

BRIEF DESCRIPTION OF THE DRAWINGS AND DETAILED DESCRIPTION OF THE INVENTION

In general, the x-ray film processor checker of the present invention, also referred to as an x-ray densitometer, in the preferred embodiment of the present invention, measures three exposed areas on a strip of x-ray film and compares their density with pre-set limits. Combinations of these comparisons illuminate appropriate combinations of light emitting diodes on the front panel of the unit indicating the operational status of the processor used in developing the film. The range of densities covers approximately three orders of magnitude and the desired precision of measurement is approximately ½ of 1% of the density measured. In accordance with the present invention, this is accomplished by a unique ratiometric measurement system.

This ratiometric x-ray densitometer continuously establishes a 100% transmission point when no film is in the reader. When a film strip is detected entering the reader, the 100% transmission level is stored by a sample and hold circuit. The four density levels are established by a precision resistor divider from the 100% transmission reference. The photo current created by the density being measured is compared to a reference current from the precision divider string by the same operational amplifier used in setting the 100% transmission level, compensating for long term drifts in the measuring circuit. The only accuracy determining considerations in the circuit are the stability of the precision resistor divider network, the short term drift of the operational amplifiers, the linearity of the photo detector, and the drift of the sample and hold circuit. The drift of the precision resistor divider network can be made negligible by design using relatively inexpensive precision metal film resistors. The short term drifts of the operational amplifiers are negligible by design and the relatively short period that they must remain stable. The linearity of the photo detector is insured by selecting a PIN (P type—Intrinsic—N type) photo detector which has a linear range of approximately $10^{12}$ to 1. The drift of the sample and hold circuit is also rendered negligible by design and is guaranteed by limiting the time the sample must be held with an abort timer. All other variations are effectively canceled by the ratiometric technique. These include source intensity, power supply drift, and other component drifts. It also should be noted that no external reference is required for the operation of the circuit. The reference voltage is the 100% transmission level that is generated immediately before each measurement.

Figure 1:
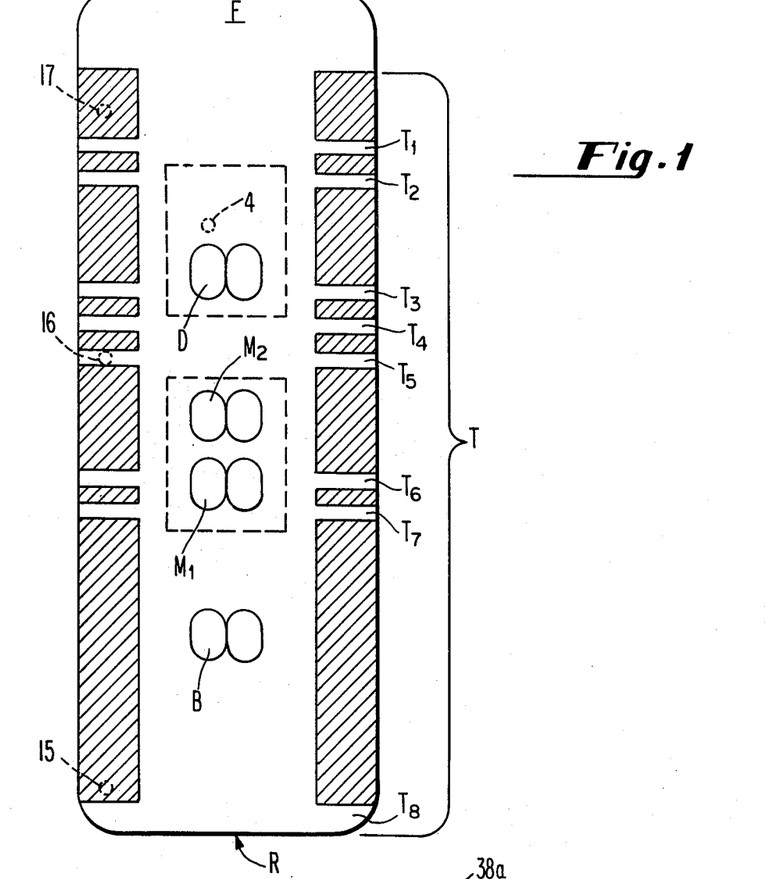
FIG. 1 is a layout view of a film test strip in accordance with the present invention.

In accordance with the preferred form of the present invention, a method and apparatus are utilized which are specifically adapted to a test film strip having graded density areas arranged in a linear sequence associated with timing signal means in the same film. More particularly, as illustrated in FIG. 1, the film strip typically consists of a linearly oriented strip F having three graded density areas (of preselected and predetermined density, assuming proper operation of the processor), identified as the unexposed or base fog area B, the medium or mid-range density area having two test area sites $M_1$ and $M_2$, and a dark area D. Graded density area B is also referred to as the "base fog" check point. This area of the film is unexposed, as compared to areas M and D which are exposed to different preselected X-ray density levels, related to preselected signal outputs in the test apparatus of the present invention.

Film strip F is adapted for sequential testing of areas B, $M_1$, $M_2$ and D with reference to the leading edge R of the film by timing means T. In the preferred embodiment of this invention, timing means T consists of dark strips with adjacent spaces $T_1$, $T_2$, $T_3$, $T_4$, $T_5$, $T_6$, $T_7$, and $T_8$, each of which provide an output signal in a photodetector circuit indicative of the position of the film in the test apparatus of the present invention relative to graded density areas B, $M_1$, $M_2$, and D. In operation, film strip F is inserted in a slot or channel in an apparatus adapted to test a film strip as disclosed and claimed herein, until leading edge R reaches a reference point for start of the test, such as a forward stop or edge of the film slot or channel. At this time, graded density area sensing photodetector 4 and timing sequence photodetector 15, 16 and 17 (together with their associated light sources) are positioned to "read" the film at the positions indicated in FIG. 1. While the film strip is moved through (or pulled from) the apparatus, the photodetector 4 with its associated circuitry tests each of the graded density areas D, $M_2$, $M_1$, and B sequentially, the sequence of testing and readout of test results being synchronized by timing means T, together with photodetectors 15, 16 and 17 and their associated circuits.

Figure 2:
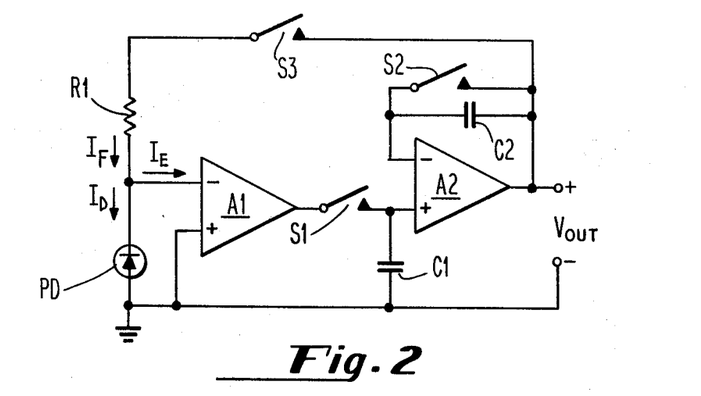
FIG. 2 is a circuit diagram depicting, for explanation purposes, an elementary version of the analog circuitry of the actual photodetector circuit shown in the schematic diagram of FIG. 5.
Figure 5:
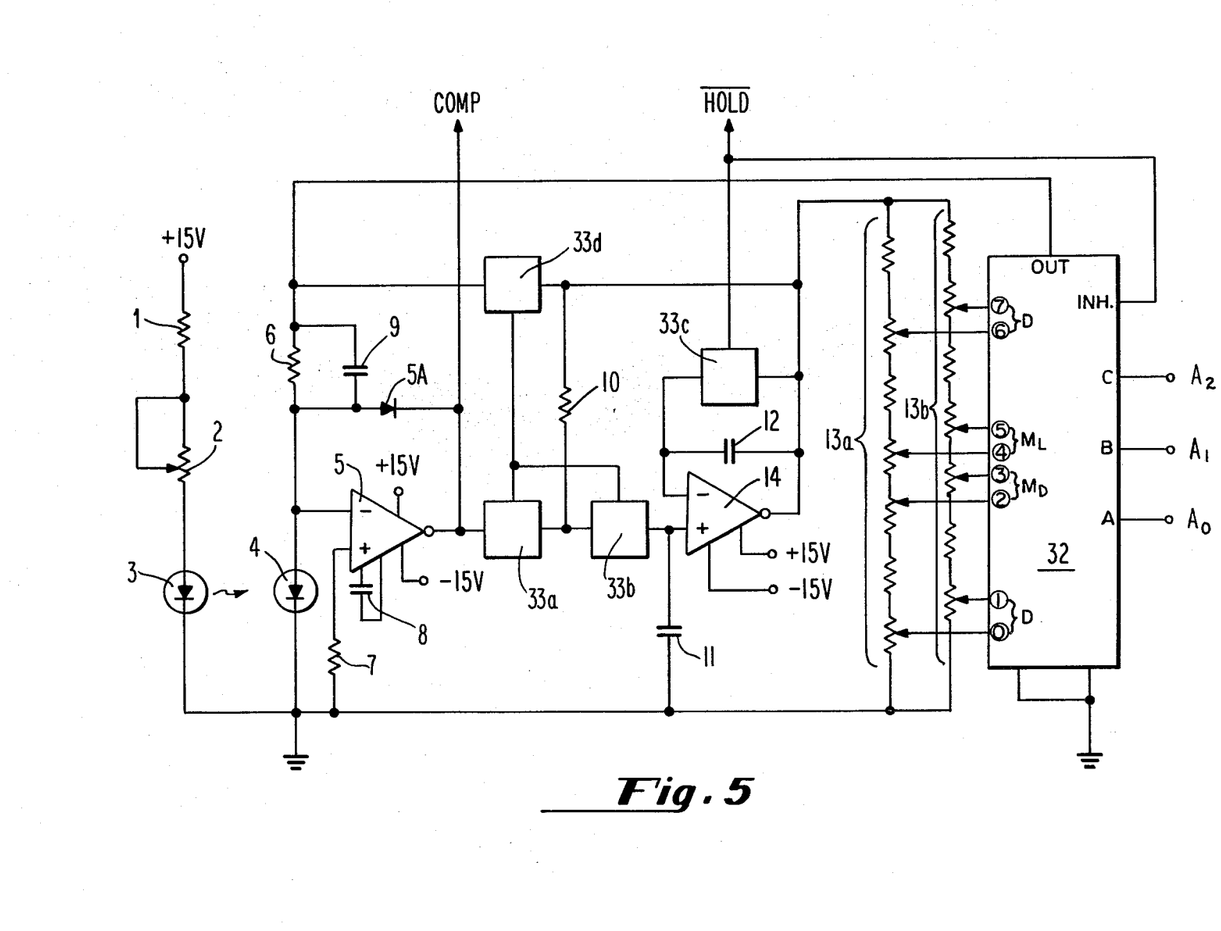
FIG. 5, as indicated previously, is a schematic diagram of the photodetector circuit of the present invention.

To aid in understanding of the analog circuitry in the preferred embodiment of apparatus in accordance with the present invention, reference may be made first to FIG. 2, which depicts an elementary version of the analog circuitry as shown in the schematic diagram of the photodetector circuit, as shown in FIG. 5. Referring to FIG. 2, photodetector PD generates a current $I_D$ proportional to the light intensity falling on it. The feedback or reference voltage is converted to a current by resistor R1. The difference between the light induced current $I_D$ and the reference or feedback current $I_F$ is amplified by amplifier A1. Switches S1 and S2, capacitors C1 and C2, and operational amplifier A2 form a first order sample and hold circuit inside the feedback loop of amplifier A1. Since amplifier A2 is inside the feedback loop of amplifier A1, the accuracy of the sampled voltage is primarily determined by amplifier A1 which is a precision, low drift, bipolar operational amplifier. Therefore, amplifier A2 can be selected with characteristics that minimize the drift of the sample and hold circuit without regard to DC accuracy.

The switches S1, S2 and S3 are complimentary MOS analog switches which are controlled by the logic portion of the unit.

Figure 3:
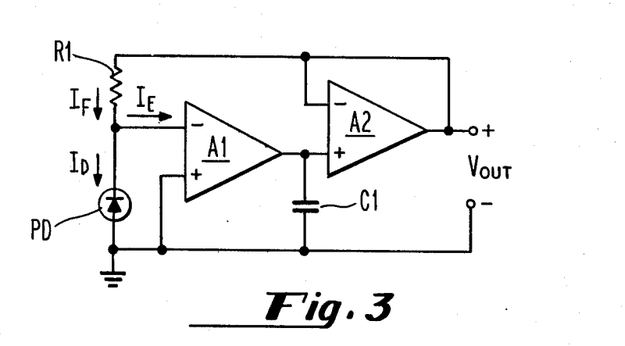
FIG. 3 illustrates the circuit of FIG. 2 in the sample mode.

FIG. 3 shows the circuit of FIG. 2, in the sample mode. All three switches are closed* in the sample mode and will be considered to be ideal switches with no series resistance. In reality, the switches do have a finite series resistance which has no effect on the circuit operation other than affecting the settling time, in the case of switches S1 and S2. In the case of switch S3 there is negligible effect since the switch resistance is many times smaller than resistor R1. It is a fundamental property of an operational amplifier connected in a negative feedback loop that the amplifier will maintain an output voltage that forces the voltage between the plus and minus inputs of the operational amplifier to be zero and, therefore, the current into the minus input to be zero. Therefore, if the current $I_E$ equals zero, the photo current $I_D$ must equal the feedback current $I_F$. The junction of the photo-diode and R1 must be at ground since the voltage between the plus and minus inputs of amplifier A1 must be zero. Therefore, the voltage across R1 will equal $I_F$ times R1, which is also equal to $I_D$ times R1. The voltage across R1 will be equal to $V_{out}$. Since the gain of amplifier A2 is equal to one, the voltage across C1 must also equal $V_{out}$.

*(and therefore, along with short circuited capacitor C2, are omitted from FIG. 3).

Figure 4:
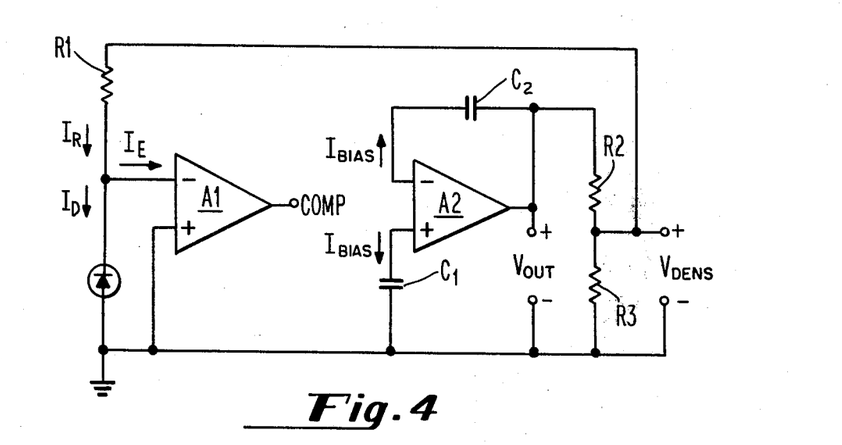
FIG. 4 shows the circuit of FIG. 2 in the hold mode.

When the circuit switches to the hold mode, the circuit of FIG. 2 can be redrawn as FIG. 4. In the hold mode, switches S1 and S2 are opened to present a nearly infinite impedance*. Amplifier A2 is a field effect input device and exhibits an extremely small input current and a very high input impedance. Therefore, the voltage stored on capacitor C1 remains at $V_{out}$. Since amplifier A2 has a gain of plus one its output voltage $V_{out}$ equals the voltage on capacitor C1 and will drift very slowly, mainly due to the bias current on the inputs on amplifier A2 and the self leakage of the capacitor. At nominal room temperatures the rate of drift is approximately ½% in six minutes. This rather high performance is achieved by careful component selection and a compensating circuit including capacitor C2. For the first approximation capacitor C2 is considered identical to capacitor C1 and the bias currents out of both the plus and minus inputs of amplifier A2 are considered to be identical. Therefore, the voltage change on each capacitor would be identical and would subsequently cancel each other. In reality, the matching of the capacitors and the bias currents is on the order of 10%, so an improvement of about a factor of 10 is achieved using this scheme.

*(again the schematic diagram of FIG. 4 omits showing switches S1, S2, and S3 as such).

The output of amplifier A2, which is the 100% transmission level, is now divided down by the precision resistor string modeled as resistors R2 and R3 for simplicity. However, in reality R2 and R3 may be many resistors, both fixed and adjustable, connected in series. The voltage at the junction of R2 and R3 is equal to $V_{out}$ times R3 divided by the quantity R2 plus R3 and depends only upon the ratios of the resistors. The voltage corresponding to the desired density limit is converted into a current by resistor R1. This reference current or $I_R$ is equal to $V_{dens} = V_{out} \times R3/(R2+R3)$ provided that the parallel combination of R2 and R3 is much smaller than R1, which is assured by design. The current $I_D$ is generated by the photo-diode which is proportional to the actual density being measured. The difference between the reference current and the photo current is $I_E$ which is fed into the input of amplifier A1. The negative feedback loop is not completed around amplifier A1, but amplifier A1 will attempt to adjust its output to a level which would create a zero voltage across its inputs. This results in a "logic one"* if the current $I_E$ is less than zero, or a "logic zero" output if the error current is greater than zero. Therefore, the output of A1 will be a "logic one" if $I_D$ is greater than $I_R$ or, in other words, if the density is less than the reference density. The output of A1 will be a "logic zero" if $I_D$ is less than $I_R$, or similarly, if the density is greater than the reference density.

*NOTE: A reference to a "logic one" is the same as a "true" condition which in the case of this circuit is the most positive voltage (+15 volts). Conversely, a "logic zero" is the "false" condition and the most negative voltage (ground).

Figure 8:
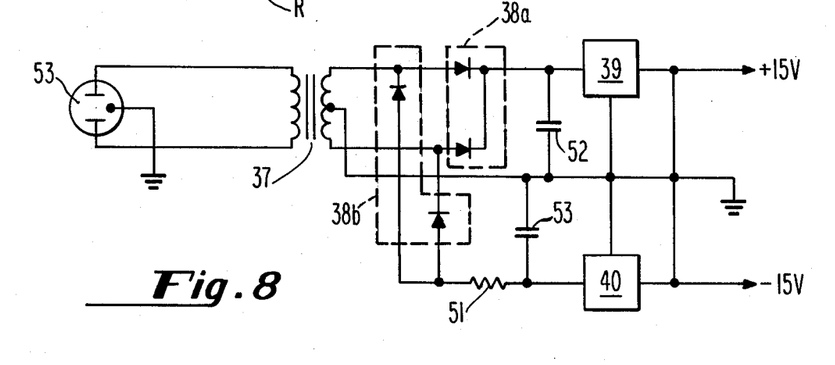
FIG. 8 is a circuit diagram of the power supply circuit in the preferred embodiment shown in the previous figures.

The details of the actual photodetector circuit in the preferred apparatus of the present invention are shown in the schematic diagram of FIG. 5. The light source consists of a gallium arsenide, infrared, light emitting diode powered from a plus 15 volt supply (the details of which are shown in FIG. 8) through a current limiting resistor 1 and a rheostat 2. The function of rheostat 2 is to establish the 100% transmission level at the high end of the circuit's operational range allowing for degradation in the light emitting diode and dust and dirt in the reader assembly. This adjustment also compensates for the manufacturing tolerances on the light output of light emitting diode 3 and the sensitivity of the PIN photodetector which consists of a PIN photo-diode 4 operating in the zero-voltage mode to minimize nonlinearities and to nearly eliminate the dark current effect. Amplifier A1 (as seen in FIG. 2) is an LM308A precision operational amplifier 5. It is powered from the plus and minus 15 volt supply, which allows its output to swing all the way to ground. A FD333 low leakage diode 5A from the negative input of amplifier 5 to the output prevents the output of the amplifier from swinging more than about 25 millivolts below ground for any reasonable circuit conditions. A 100K ohms, 1% precision metal film resistor 6 connected to the negative input of amplifier 5 corresponds to R1 as shown in FIG. 2. An identical resistor 7 is connected to the positive terminal of amplifier 5 as a first order compensation for the bias currents of the operational amplifier 5. Its principle of operation is the same as the bias compensation scheme used on the sample and hold circuit. If the bias currents are assumed to be equal, they produce equal voltage drops in the 100K ohm resistors and cancel each other. The 30 picofarad capacitor 8 on amplifier 5 provides closed loop frequency compensation and the 470 picofarad capacitor 9 across the resistor 6 compensates for the lag induced by the first order sample and hold circuit.

Switch S1 (as shown in FIG. 2) actually consists of two sections 33a and 33b of a CD4016 quad analog switch 33 (shown in FIG. 5 as elements 33a, 33b, 33c, 33d). These sections 33a and 33b of this switch, each of which can be considered a single switch, are connected in series with a one megohm reference resistor 10 to their center point. In the hold mode, when both switches 33a and 33b are off, the voltage on the 0.47 microfarad sample capacitor 11 referenced to ground is approximately $V_{out}$ and the voltage between the two switch sections is driven to approximately $V_{out}$ by the one megohm reference resistor 10. Since a nearly zero voltage is impressed across the switch between sample capacitor 11 and reference resistor 10, even if the off resistance of the switch is not infinite, only a very small current could flow. Another section 33c of quad analog switch 33 performs the functions of S2 (as seen in FIG. 2) in shorting out the 0.47 microfarad compensation capacitor 12 in the sample and hold circuit. The voltage across this switch section 33c is also nearly zero in the hold mode, since the initial voltage across the compensating capacitor 12 is zero; therefore, its leakage is also rendered negligible. In fact, since switch elements 33a, 33b and 33c of switch 33 between sample capacitor 11 and the reference resistor 10 are in the same package and operate under virtually identical conditions, any leakage will be approximately equal in magnitude and therefore would cancel in the same manner as the bias current. Switch S3 (as seen in FIG. 2) is implemented using the last quarter 33d of quad analog switch 33; its leakage is not a factor since the switched side of the 100K ohm resistor 10 is always driven from a low impedance source.

The precision resistor strings 13a and 13b are connected to the output of the sample and hold amplifier 14, an LF 355N FET input operational amplifier. The various reference levels from the precision reference divider are selected by a CD4051 8-input analog multiplexer 32. The 8-input analog multiplexer is just a combination of 8 analog switches similar to those found in the quad analog switch, which can be addressed one at a time through three address lines $A_o$, $A_1$, and $A_2$ in a binary sequence. All eight switches share a common terminal on one side labeled "out"; therefore, depending on the address applied to the A, B, and C inputs, the binary equivalent switch is closed and routes its appropriate reference voltage to the "out" pin. In the current circuit implementation, there are two precision reference strings 13a and 13b to accommodate different film processor combinations; the appropriate reference string is selected by the high order address of the 8-input multiplexer by switch S4 (FIG. 6) which places either a logic "zero" or "one" on address line Ao by grounding the 15 volt potential normally present through resistor 48.

Figure 6:
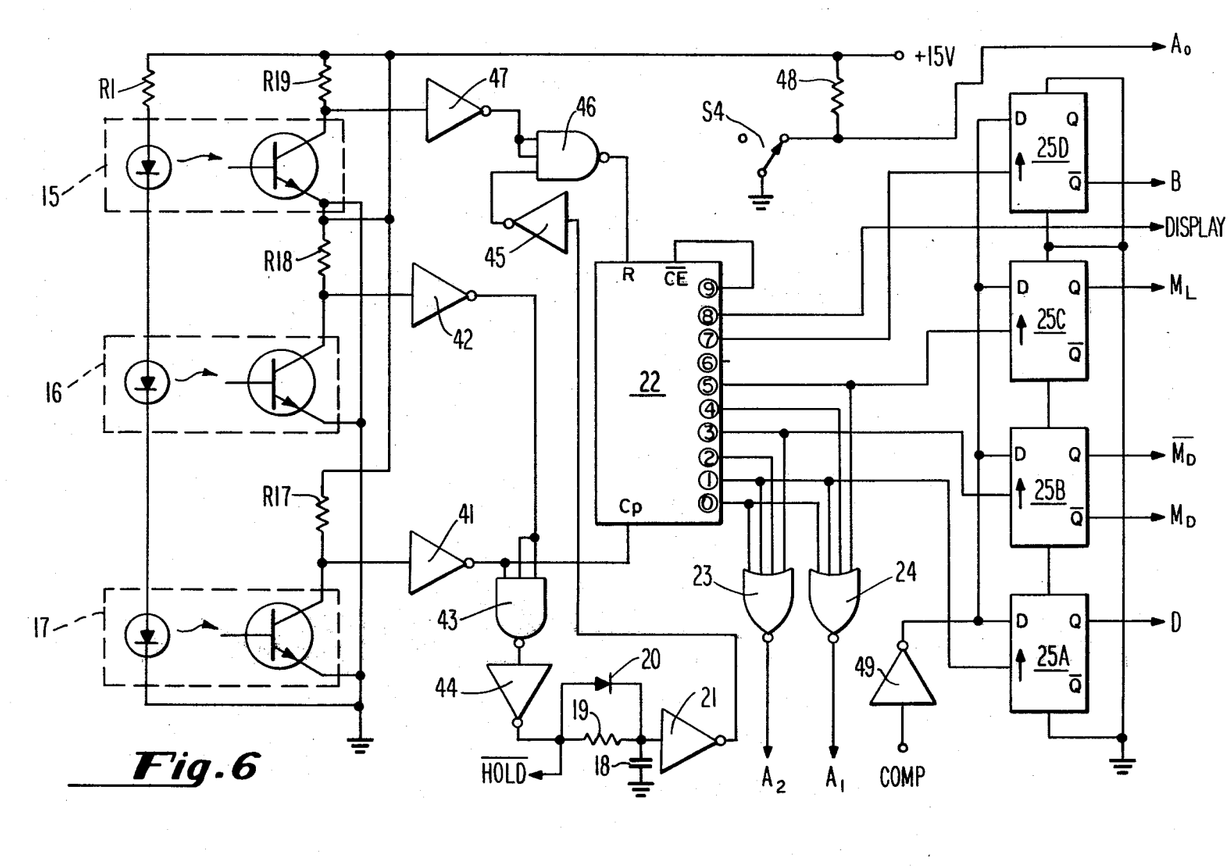
FIG. 6 is a schematic diagram showing the major components of the sequencing circuitry in the x-ray processor test apparatus of the preferred embodiment of the present invention.

Referring to FIG. 6, there is shown a schematic diagram, comprising the sequencing circuitry for the densitometer of this invention in its preferred apparatus embodiment. Three light emitting diode and phototransistor pairs 15, 16, and 17 detect timing marks ($T_1$–$T_8$ in FIG. 1) placed on the side edge of test film strip (F as seen in FIG. 1). Photodetector 17 detects when film has begun to enter the reader and actually reads the timing marks on the film and advances the CD4017 decade counter 22 when a timing mark is encountered. Photodetector 15 detects when the film has been fully inserted into the reader, i.e., has bottomed. Photodetector 16 complements photodetector 17 in also indicating, when it is covered, that film is in the reader. This is important in order to keep the circuit in the hold mode when photodetector 17 is uncovered (i.e., is exposed to a non-dark timing mark $T_1$–$T_8$).

Before walking through an actual measurement sequence, an explanation of the timing track is in order. The first consideration in the timing track design is that the film detector light path or the timing detector light path must be blocked before any part of the film covers PIN diode 4 (FIG. 5). Another consideration is that either the film detector 16 or timing detector 17 must be blocked when film is in any position in the reader. The third consideration is that the "bottom" detector 15 only be covered when the film is fully inserted in the proper direction so that timing marks ($T_1$–$T_8$ in FIG. 1) must be appropriately positioned in relation to the patterns on the film; this positioning will become more apparent as the circuit operation is explained.

With film detector 16 and timing detector 17 uncovered (prior to insertion of that film strip 10), the hold signal will be a "logic one" placing the analog circuit in the sample mode. Therefore, the analog circuit is continuously updating the 100% transmission reference voltage. As soon as the film detector or timing sensor is covered, the hold signal will go to a "logic zero", placing the analog circuitry into the hold mode through Schmidt trigger inverters 41 and 42, NAND gate 43, and inverter 44. At this time, the abort timer consisting of a 4.7 microfarad tantalum capacitor 18, a 4.7 Megohm resistor 19, a 1N4446 diode 20, and a Schmidt trigger inverter 21 start to time. If the circuit remains in the hold mode for more than approximately twenty seconds, the output of Schmidt trigger 21 will go to a "logic one" forcing the decade counter 22 to reset, through inverter 45 and NAND gate 46, and the sequence to be aborted.

Assuming the abort timer has not timed out, as film strip F is inserted further, timing detector 17 will deliver pulses to the clock input of the decade counter 22 through Schmidt trigger inverter 41. These pulses cause the counter to count until it reaches its ninth count, at which time the clock input will be disabled through the count enable input. The counter is reset to "zero" when the "bottom" detector is covered placing a "logic one" on the reset pin through Schmidt trigger inverter 47 and NAND gate 46. When the film has bottomed and reset decade counter has not timed out, the logic circuitry is in a known state with the "zero" output of the decade counter 22 at a "logic one" state. The "zero" output of the decade counter 22 is decoded by two four-input NOR gates 23 and 24 which convert the decimal "zero" to the binary equivalent on address lines A1 and A2. Address lines A1 and A2 will both be "logic zero", selecting the lowest tap on the precision reference chain 13a or 13b which corresponds to the highest density portion on the film. At this time the highest density portion D of the film is also positioned between the infrared source 3 and the photo-diode 4. As the film is withdrawn, the first timing pulse triggered by timing mark T1 causes the decade counter 22 to advance one count. The "zero" output goes to a "logic zero" and the "one" output goes to a "logic one" state. The quad NOR gates 23 and 24 decode the "logic one" state on the "one" output to the address zero, which keeps the lowest tap on the reference chain 13 selected.

The positive transition from low to high on the "one" output of the decade counter also clocks a D type flip-flop whose D input samples the output from amplifier 5 through Schmidt trigger inverter 49 which compares the reference current to the photocurrent for the most dense segment. Therefore, the state of the amplifier 5 is sampled and stored in a D type flip-flop 25A, and this becomes the D term (dark area acceptable or too light) in the display logic indicating the results of the comparison of the most dense section D of the film strip F. As the film is withdrawn further, another timing mark $T_2$ is encountered and the decade counter 22 advances to the "two" state. The quad NOR gates 23 and 24 decode this number into 01 (binary) address which corresponds to the next higher tap on the precision divider chain. This tap generates an output signal, which is compared to the medium density dark-side threshold level. This output signal is based on a reading of the medium density portion $M_2$ on film strip F. The next timing mark $T_3$ encountered advances the decade counter 22 to the "three" state which decodes to the same multiplexer address as the "two" state. The positive transition of this output also clocks another D type flip-flop 25B sampling the comparators output based on the medium density area $M_2$ of the film F and the medium dark-side threshold level. This is the $M_D$ term (medium density area acceptable or too dark) for the display logic. The next timing mark $T_4$ encountered advances the decade counter to the "four" state which selects the next tap up on the precision resistor divider network 13. This is the threshold for the medium light-side density level, which is compared to the test output measured on medium density area $M_1$ of the film. The next timing mark $T_5$ causes the decade counter to advance to the "five" state with no change in the multiplexer address. It also checks the medium light-side threshold comparison results (medium density area acceptable or too light) into a D type flip-flop 25C on the positive transition. This is the $M_L$ term for the display logic. The next timing pulse signaled by mark $T_6$ advances the counter to the "six" state which enables the upper-most tap on the precision resistor divider chain 13 (which provides an output comparison for the threshold of the base fog area) and causes positioning of the area B of the film under photodetector 4. Further movement of the film encounters another timing mark $T_7$ which advances the counter to the "seven" state which causes no change in the multiplexer address but causes the B area comparison to be latched in a D type flip-flop 25D which generates the B term (light area acceptable or too dark) to the display logic. On a good read pass, one more timing mark $T_8$ will be encountered which is in reality the end of the timing track. This will advance the counter to the "eight" state. When the "eight" state of the counter is reached the display line goes to a logic "one" enabling the light emitting diode display. Therefore, if less than seven timing pulses are detected, no display will result and if more than seven timing pulses are detected, the counter will advance to its "nine" state, disabling the display line and also disabling any further counting of timing marks through the clock enable input to the decade counter. The common cause of excessive timing counts would be reversal of the film direction during the film withdrawal, which would yield an incorrect reading if the display were not blanked when detecting the excess number of counts. An insufficient count condition would also yield an incorrect reading if the logic did not prevent it. The most likely cause is either a defective track or extremely rapid withdrawal of the film; however, the latter case is nearly impossible in practice.

Figure 7:
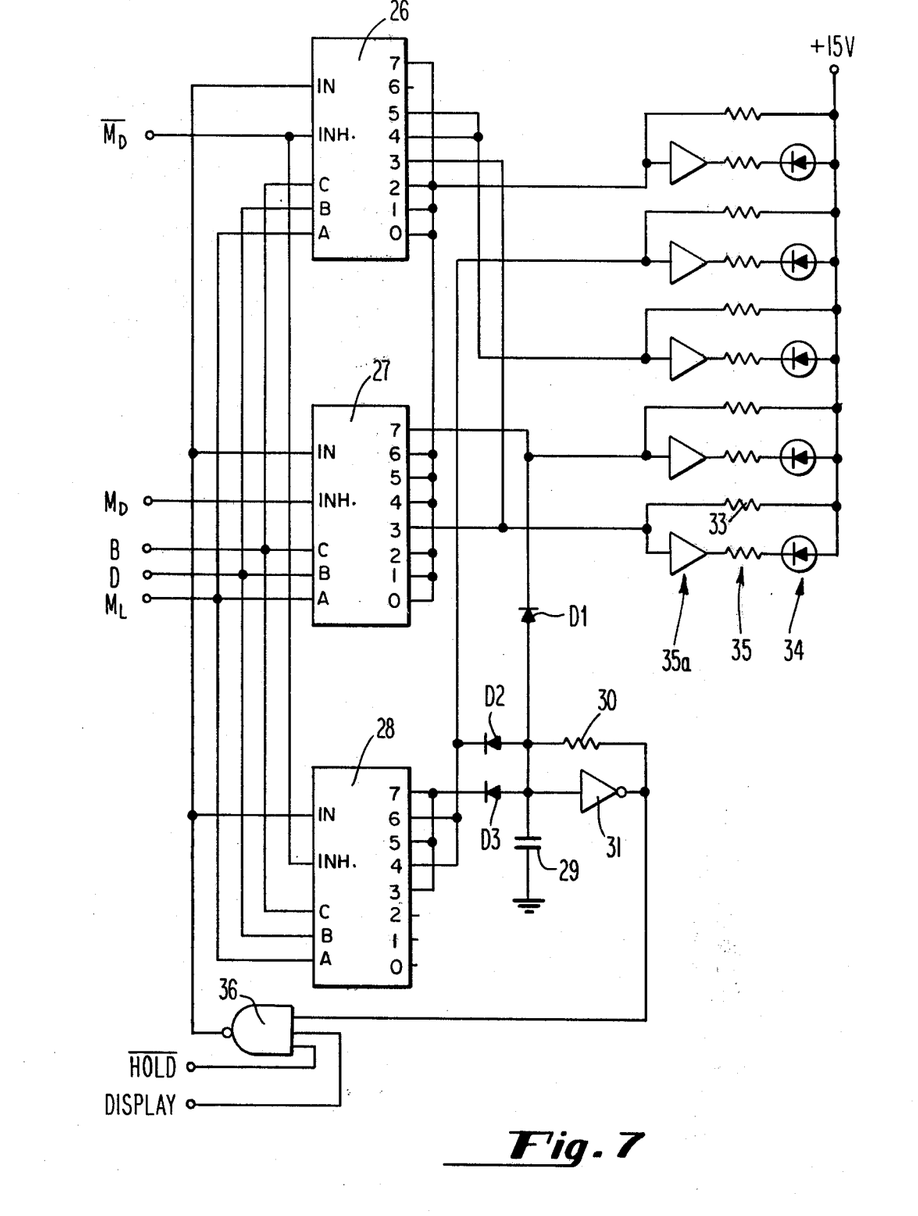
FIG. 7 is a schematic diagram of the decode logic and circuitry for the output indications in the apparatus of the preferred form of the present invention.

Once the film is completely withdrawn, the decode logic in FIG. 7 of the schematic diagram decodes the results of the four threshold measurements and lights the appropriate light emitting diodes on the front panel, provided the right number of timing marks were counted. The sample and hold circuit reverts to the sample mode where the 100% reference value is being continuously updated and the display will remain until a new test film strip F is inserted. The comparisons are decoded using eight input multiplexers 26,27 and 28 to implement the required and/or combinations. Since some of the states require flashing, a simple relaxation oscillator is constructed using a 0.47 microfarad capacitor 29, 1.2 Megohm resistor 30, and a Schmidt trigger gate 31. The flashing is gated on by unclamping the capacitor voltage with the lower eight input multiplexer. The logic was synthesized using a truth table, or Karnaugh map (see *The Design of Digital Systems*, John B. Peatman, McGraw-Hill, N.Y., 1972, pg. 63), of the desired logic and grouping the common states. Analysis of the operation of the circuit is best performed by making a table of all the possible combinations of D, $M_D$, $M_L$, and B and applying them to the appropriate inputs of the schematic in FIG. 7. The connection will be established between the input of the multiplexers 26,27 and 28 and the appropriate output as addressed by the address inputs A, B, and C on the multiplexer, where A is the least significant address bit and C is the most significant address bit. When the inhibit input is a "logic zero", all the switches are open. When a switch is open to one of the light emitting diode buffers, the input to the buffer is pulled up to plus 15 volts via 100K resistor 33. The buffers are non-inverting so the cathode end of the light emitting diode 34 is driven to plus 15 volts, which causes no current flow through the diode. To turn the light emitting diode on, the input to the buffer must be connected to a "logic zero" level or ground to drive its output low. Current would then flow from the plus 15 volt supply through the light emitting diode and through the 820 ohm resistor 35 out through the buffer output 35a to ground. A combination of the hold signal and display implemented via the input NAND gate 36 is utilized to turn all of the light emitting diodes off until a valid reading is obtained.

The last part of the circuit is the power supply which is shown in FIG. 8. The nominal 115 V, AC line input 53 is stepped down to 40 VAC by a small center tapped, transformer 37. A raw DC voltage (approximately 22 volts) of both positive and negative polarity is produced by a pair of full-wave, center tap, rectifier circuits 38a and 38b. The raw DC voltages are regulated to positive 15 V and negative 15 V utilizing conventional integrated circuit regulators 39 and 40, dissipation limiting resistor 51, and filter capacitors 52 and 53. Due to the superior supply voltage rejection of the operational amplifiers and the lack of a voltage reference requirement in the circuit operation, the required regulation is not high. The main reason for going to a regulated power supply is to prevent abnormally high operational voltages on many of the components. Therefore, a very simple approach is utilized.

As to the method of calibration of the prototype unit, since an adequate collection of transmission standards were not available, a statistical method based on some prototype film strip densities measured by another photodensitometer were employed. The prototype ratiometric photo densitometer of this invention was arranged to operate as a standard photo densitometer by removing the sample and hold circuit and completing the feedback around amplifier A1 through R1. Each density was measured using this technique and then a logarithmetric regression analysis was performed to correlate the densities measured by both devices. A theoretical equation for the output voltage of amplifier A1 as a function of density was obtained. The correlation coefficient of this equation was 0.99972, which lends a high degree of confidence to the technique. The theoretical equation is $V_{out} = 10^{-1.20777 \times density}$. From this equation the voltages at each tap in the reference divider were calculated. The output of A1 was then adjusted to 10.87 volts using the 1K rheostat 2 in series with the IR light emitting diode 3 and each tap was adjusted to its appropriate voltage using a digital voltmeter. This equation may be used to calibrate the unit to other density levels within the range.

As will be noted in FIG. 1, in the preferred form of the present invention, graded density read areas B, M and D are slightly offset from the center line of film stip F and timing strips $T_1$–$T_8$ are located along both side edges of film strip F. Preferably, graded density read areas B, M and D are elongated along the length of film strip F so as to minimize the possibility of signal distortion if the strip is pulled too quickly past a photodetector.

Preferably also, with the photodetector and graded density read areas slightly offset from the center line of film strip F, the read apparatus and film strip are adapted for a second test of a single film strip, in order to confirm the first test, particularly where some malfunction is indicated in the first test. For this purpose, identical graded density read areas are located adjacent to each of the read areas B, M and D and offset an equal distance to the other side of the center line of film strip F. Retest of the same film strip then is accomplished by turning the film strip upside down and putting it through the apparatus again. An identical result confirms the first reading while a different result indicates possible system malfunction or a localized defect in the film strip, which may then be confirmed by processing a second film strip and retesting the second film strip. The identical graded density read areas referred to for this purpose are shown in FIG. 1 but are not designated other than by their location adjacent each of the graded density test areas referred to.

While this invention has been described with respect to particular features and embodiments thereof, it should be understood that it is not limited thereto. Therefore, the appended claims should be construed to encompass the invention throughout its true spirit and scope and also to encompass not only the embodiment shown but also to encompass such modifications and variations of the invention as may be devised by those skilled in the art without departing from the true spirit and scope thereof.

We claim:

1. In a method for determining the status of a photographic film processor said method including the steps of
  a. exposing a test pattern on the film to produce, upon development, at least three test areas comprising a high density area, a medium density area and an unexposed base fog area
  b. developing said film in said processor
  c. measuring the density of said high density area portion of the film with a density measuring means in which said film is received to determine if it is too light, or acceptable; measuring the density of the base fog area to determine if it is too dark or acceptable; measuring the density of the medium density area to determine if it is too light, too dark, or acceptable
  d. logically operating upon the results of step (c) by utilizing said results as inputs to logic circuitry to produce the output indications indicative of the operational status of the film processor, the improvement consiting of: determining a first reference output signal strength of the density measuring means with no film received therein; determining additional reference output signal strengths ratiometrically related to said first reference signal strength, said additional reference signal strengths being indicative of predetermined limits of densities of said film test areas; and measuring said film test area densities sequentially with a single density measuring means and comparing the densities measured thereby with said additional reference output signal strengths.

2. In an apparatus for determining the status of a processor of photographic film, upon which film a test pattern has been exposed under calibrated conditions to produce, upon development, test areas which include a dark or high density area, an area of middle density, and an unexposed base fog area, said apparatus comprising
  a. density measuring means to measure the density of the test film in said high density area, said medium density area, and said base fog portion of the film and to produce an output signal indicative of and dependent on said density,
  b. means to compare the output signals of the density measuring means to threshold output signals for each of the three areas under nominal conditions, and
  c. means to operate upon the output signals of said density measuring means to produce a test result indicative of the operational status of said film processor, the improvement wherein: said density measuring means consists of a single means for sensing said densities and for producing output signals indicative thereof; and means are provided for sequentially testing said test areas with said single means for sensing density and for producing output signals indicative thereof.

3. The improved apparatus as recited in claim 2, further including sequential comparison means for comparing output signals from said density measuring means to selected output signal strengths, each indicative of a preselected density level and determined by a ratiometric proportioning means which establishes said selected output signal strengths in relation to a zero point output signal strength.

4. The improved apparatus as recited in claim 3, wherein said zero point output signal strength is determined as the density measuring means output signal at the 100% transmission level.

5. The improved apparatus as recited in claim 4, wherein said density measuring means comprises a light source and associated photodetector, the output of which is a current signal, and said ratiometric proportioning means comprises a network of precision resistors adapted to determine current levels ratiometrically proportioned to said current signal at the 100% transmission level and corresponding to current signal levels indicative of preselected densities.

6. The improved apparatus as recited in claim 5, wherein said sequential testing means comprises: position determining means for determining at one point in time, which of said film test areas is in position for density measurement; and comparison means for comparing said output signal, at the same point in time, to an output signal strength level corresponding to a preselected density limit of the test area then in position for density measurement.

7. The improved apparatus as recited in claim 6, in combination with a test film having a plurality of density test areas at preselected locations on said film and also having position indicating means for indication of which of said test areas is in position for density measurement, said position indicating means adapted to signal said position determining means.

8. The improved apparatus and test film as recited in claim 7, wherein said test areas are disposed on a line, said apparatus and film being adapted to permit movement of said film along said line in the course of testing said film, said film also including said position indicating means disposed along the same or a parallel line.

9. The improved apparatus and test film as recited in claim 8, wherein: said position indicating means comprises signal areas on said film at preselected locations relative to said test area locations; and, said position determining means comprises a light source and associated photodetector, the output of which is connected to trigger a counting means, said counting means including a test set means indicative of the start of a test sequence.

10. The improved apparatus and test film as recited in claim 9, said counting means also including signaling means to signal a test output when the proper number of signal areas have been detected or to preclude a test output when more or less than the proper number of signal areas have been detected following the setting of said test set means within a preselected time limit.

11. The improved apparatus and test film as recited in claim 10, wherein said test area and said portion indicating means are adapted for testing two identical sets of signal areas and said sequential testing means is adapted to compare the output signal produced in testing each of said identical areas separately to a high density limit and to a low density limit corresponding to said test area density.

12. The improved apparatus and test film as recited in claim 10, wherein: said apparatus includes a slot for receiving said test film; said test set means comprises a contact indicator of contact made between a leading edge of said film and the inner end of said slot, whereby said start of test sequence is initiated upon full insertion of said test film in said slot; and, said test sequence proceeds as said film is pulled from said slot.

13. The improved apparatus as recited in claim 2, wherein said sequential testing means comprises: (a) position determining means for determining, at one point in time, which of said film test areas is in position for density measurement; and (b) comparison means for comparing said output signal at the same point in time, to an output signal strength level corresponding to a preselected density limit of the test area then in position for density measurement.

* * * * *